(12) United States Patent
Chitre et al.

(10) Patent No.: US 6,792,318 B2
(45) Date of Patent: Sep. 14, 2004

(54) TECHNIQUE FOR FIXATING A LEAD

(75) Inventors: Yougandh Chitre, Valencia, CA (US); Kerwyn Schimke, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 204 days.

(21) Appl. No.: 10/172,193

(22) Filed: Jun. 13, 2002

(65) Prior Publication Data

US 2003/0233139 A1 Dec. 18, 2003

(51) Int. Cl.[7] ............................................. A61N 1/00
(52) U.S. Cl. ..................................................... 607/126
(58) Field of Search .................. 604/175; 607/116–138; 623/23.74

(56) References Cited

U.S. PATENT DOCUMENTS

| | | | |
|---|---|---|---|
| 3,902,501 A | | 9/1975 | Citron et al. ................ 128/418 |
| 4,135,518 A | * | 1/1979 | Dutcher ....................... 600/374 |
| 4,149,542 A | * | 4/1979 | Thoren ........................ 607/121 |
| 4,913,164 A | | 4/1990 | Greene et al. ............... 128/785 |
| 5,238,007 A | | 8/1993 | Giele et al. .................. 607/126 |
| 5,318,572 A | * | 6/1994 | Helland et al. .............. 607/121 |
| 5,645,580 A | * | 7/1997 | Moaddeb et al. ............ 607/122 |
| 5,865,843 A | * | 2/1999 | Baudino ....................... 607/116 |
| 6,078,840 A | | 6/2000 | Stokes .......................... 607/127 |
| 6,161,029 A | | 12/2000 | Spreigl et al. ............... 600/381 |
| 6,216,045 B1 | | 4/2001 | Black et al. ................. 607/122 |
| 6,263,249 B1 | * | 7/2001 | Stewart et al. ............... 607/116 |
| 6,304,786 B1 | | 10/2001 | Heil, Jr. et al. ............. 607/126 |
| 6,363,286 B1 | * | 3/2002 | Zhu et al. .................... 607/120 |
| 6,584,363 B2 | * | 6/2003 | Heil et al. ................... 607/126 |
| 2002/0045926 A1 | | 4/2002 | Heil, Jr. et al. ............. 607/116 |

* cited by examiner

Primary Examiner—Mark Bockelman

(57) ABSTRACT

An implantable cardiac stimulation lead system for use with an implantable stimulation device includes an elongated lead with a conductor extending between distal and proximal ends. A tubular insulating sheath overlies the conductor and has an outer peripheral surface of revolution defined by a radius originating at the longitudinal axis. A tip electrode at the distal end of the lead is attached to the conductor. A proximal connector is in electrical continuity with the stimulation device and coupled to the tip electrode. The insulating sheath is formed with a passive fixation feature formed into the outer peripheral surface for encouraging tissue ingrowth to facilitate stability of the tip electrode when the lead system is implanted. No portion of the passive fixation feature extends radially from the longitudinal axis by a distance greater than the radius of the tubular insulating sheath.

4 Claims, 4 Drawing Sheets

TECHNIQUE FOR FIXATING A LEAD

FIELD OF THE INVENTION

The present invention relates to implantable cardiac stimulation leads having an anchoring mechanism and, more particularly, to a lead construction employing an isodiametric lead body to facilitate extraction of the lead should the need arise.

BACKGROUND OF THE INVENTION

Pacing leads using an anchoring mechanism for anchoring a distal tip with respect to the inside wall of the heart are well known and very important to a successful pacing system. Passive fixation pacing or defibrillation leads typically employ tines or fins as a means of fixating its distal end into the endocardium to prevent microdislodgment and thereby maintain relatively stable capture and sensing values. Even though tines composed of silicone rubber or other suitable material fold back on themselves when fed through an introducer at implantation, in a well-known manner, the tines tend to dictate the size of the introducer employed. In satisfying the demand in the industry for pacing and defibrillation leads and catheters with ever smaller French sizes, minimizing the overall size of future lead designs is warranted.

An early anchoring mechanism using tines is disclosed in U.S. Pat. No. 3,902,501 to Citron et al. The tined lead provides a plurality of pliant tines that extend from an area adjacent the distal tip and electrode of the lead, the tines forming an acute angle with the lead body. The tines are effective in engaging the trabeculae found in the ventricle as well as the atrium, to maintain the electrode tip in a secure position after the physician has positioned it for a good pacing threshold.

While the tined lead has been highly successful, it has carried one longstanding drawback, namely the problems associated with the lateral projections of the tines at the time of introduction of the lead and/or in attempting to reposition the lead. Basically, the lateral extension of the tines causes an effective increased diameter of the lead at about the distal tip, i.e., the effective diameter is much greater at the distal tip than it is along the length of the lead, which length has a suitable uniform small outer diameter. The tines can get wedged at the time of introduction, particularly in passing through the valve between the atrium and the ventricle for positioning against the inner wall of the right ventride. Further, once the physician has positioned the distal tip against the heart wall, it may be desirable to change that position, in either acute or chronic situations, to obtain a position which offers improved pacing threshold; or to withdraw the lead entirely. In such a situation, withdrawal of the lined anchor mechanism may be difficult, or even impossible, to do without damage to the trabeculae or to a valve.

The difficulty of introducing a pacing lead with a tined anchoring element was recognized in the above-mentioned Citron at al. patent which showed an embodiment which included a mechanism for holding the tines against the electrode body during insertion, while allowing their release once the tip was positioned in proximity to the heart wall. However, the mechanism disclosed has not been effective in achieving the aim of reducing the tip cross-section while reliably providing for release of the tines after insertion of the lead. Further, this mechanism did not have any capability of transforming the tines into a reduced cross-sectional geometry which would permit easier withdrawal of the anchor when and as desired. What remained necessary at that time, and still remains a need in the art, is a design which provides both for avoiding the lateral extension of the tines or other anchor mechanism during introduction, and also one which can withdraw the tines in such a manner as to provide improved characteristics for withdrawing the lead after it has already been positioned against the heart wall.

Since the introduction and commercial success of the tined lead, there have been a number of efforts in the pacing industry, and disclosed in the patent literature, to provide an anchoring mechanism which would provide improved characteristics for minimizing the above-noted problems at introduction and/or repositioning. A patent disclosing an extensible passive fixation mechanism for a pacing lead is U.S. Pat. No. 4,913,164 to Greene et al. This patent shows a mechanism for moving tine-type elements from a first unextended position to a second extended position, or vice versa. However, the mechanism is complex, and the technique of closing the tine-type elements would tend to ensnare the lead tip in prior-engaged trabeculae, rather than provide easy withdrawal. U.S. Pat. No. 4,957,118 to Erlebacher discloses another form of electrode lead having a tine assembly, wherein the tines can be actively moved back and forth between a retracted position and an extended position. However, the mechanism of this disclosure likewise results in a similar problem for extraction, namely the tine element is brought down over or on top of the engaging trabeculae. Further, when in the closed position, the tine end is free and provides a space between the tube casing and the tine which would snag trabeculae when the physician attempts to withdraw the lead.

In U.S. Pat. No. 5,238,007 to Giele et al., the lead has an anchoring mechanism at its tip end which in its normal state provides for fixation of the tip end to the inner heart wall and is transformable into a second state wherein the fixation mechanism is transformed to lie substantially parallel to the lead axis. In the second state, the fixation mechanism presents a reduced effective outer diameter and a substantially continuous smooth outer surface extending proximally back from the lead tip. The lead comprises a telescoping mechanism which is provided at its distal end for axial movement of a portion of the anchoring mechanism, for changing it from a normal state to a temporarily transformed state.

Despite all of the advances already achieved, as just mentioned, there remains a need in the art for a pacing lead which provides an effective anchoring mechanism when the lead is in position while having the ability to reduce the effect of such anchoring mechanism, when desired, such as during introduction or repositioning of the lead. Stated differently, there is a need for minimizing the effective cross-section of an anchor mechanism whereby the anchor mechanism is transformed to a geometry which as closely as possible merges with the cylindrical lead casing, and which does not obstruct withdrawal of the lead when in the transformed state.

It was in light of the foregoing that the present invention was conceived and has now been reduced to practice.

SUMMARY OF THE INVENTION

An implantable cardiac stimulation lead system for use with an implantable stimulation device includes an elongated lead with a conductor extending between distal and proximal ends. A tubular insulating sheath overlies the conductor and has an outer peripheral surface of revolution defined by a radius originating at the longitudinal axis. A tip electrode at the distal end of the lead is attached to the conductor. A proximal connector is in electrical continuity with the stimulation device and coupled to the tip electrode. The insulating sheath is formed with a passive fixation feature formed into the outer peripheral surface for encouraging tissue ingrowth to facilitate stability of the tip electrode when the lead system is implanted. No portion of the passive fixation feature extends radially from the longitudinal axis by a distance greater than the radius of the tubular insulating sheath.

A primary feature, then, of the present invention is the provision of an implantable cardiac stimulation lead having an anchoring mechanism and a lead construction employing an isodiametric lead body.

Another feature of the present invention is the provision of such a stimulation lead which is of isodiametric design and can be employed with an introducer of reduced French size.

Yet another feature of the present invention is the provision of such a stimulation lead in which the isodiametricity of its design will facilitate extraction should the need arise.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention illustrate one of the embodiments of the invention, and together with the description, serve to explain the principles of the invention in general terms. Like numerals refer to like parts throughout the disclosure.

BRIEF DESCRIPTION OF THE DRAWINGS

The foregoing aspects and other features of the present invention are explained in the following description, taken in connection with the accompanying drawings, wherein.

DETAILED DESCRIPTION OF THE PREFERRED EMBODIMENT

Figure 1:
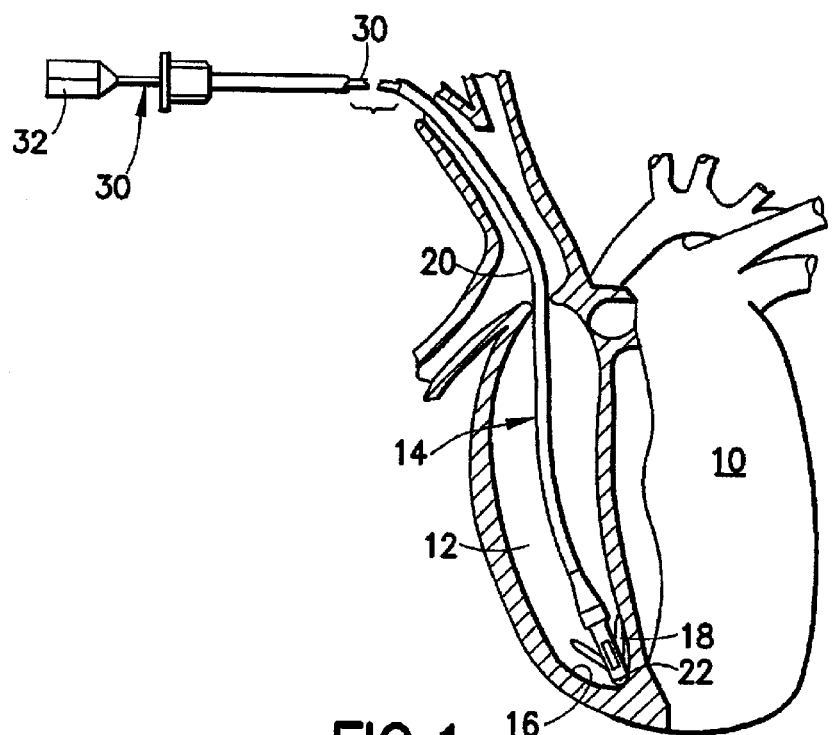
FIG. 1 is a perspective view illustrating a heart with a portion cut away to reveal a known implantable lead assembly, capable of using the invention, secured to a wall of the heart.

Referring to FIG. 1, there is shown a diagrammatic perspective view partially cut away and shown in section of a heart 10 into the right ventricle 12 of which is inserted a body implantable lead 14 of the endocardial type of a known construction. The lead 14 is attached to an interior wall 16 of the heart 10 by means of fixing tines 18 which engage the tissue or trabeculae of the heart.

Figure 2:
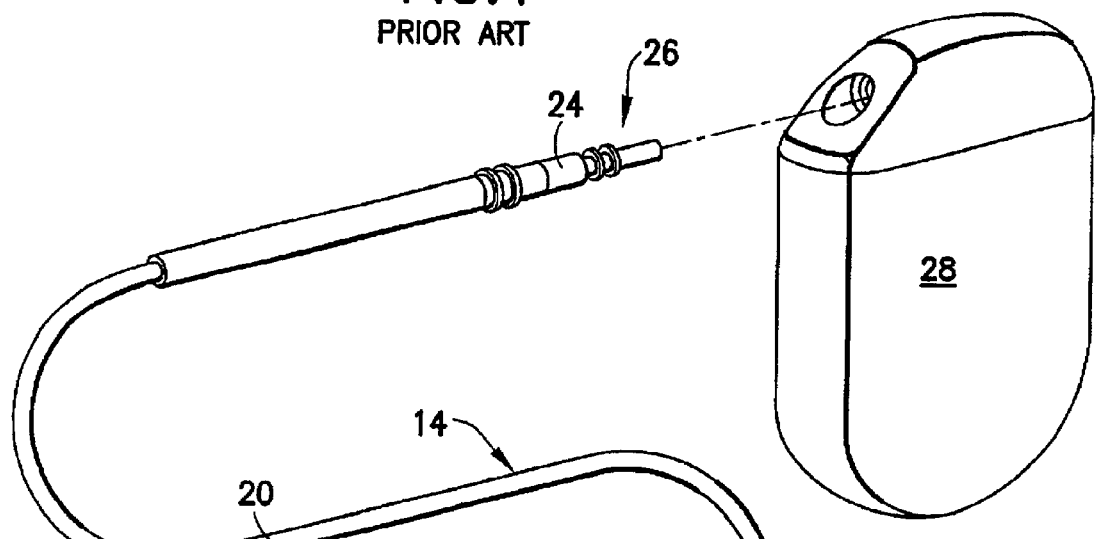
FIG. 2 is a perspective view of a known implantable lead system in combination with a stimulating device such as a pacemaker, the lead system capable of modification to use the invention.

As further illustrated in FIG. 2, the lead 14 also includes fan insulating sheath 20 interconnecting a distal electrode 22 secured adjacent the interior wall 16 and an electrical connector 24 at a proximal end 26 to which can be attached a source of electrical energy such as a pacemaker 28. In FIG. 1, an elongated stylet 30 is illustrated inserted within the insulating sheath 20 and extending through a lumen of the insulating sheath 20 between a distal attachment device (not shown) and a proximal manipulating device 32. The manipulating device is distant from the threaded tip end and may be a finger grip at a proximal extremity of the stylet 30 provided for controlling the introduction of the stylet into the lead 14 and its subsequent withdrawal. The stylet may be used to provide rigidity to the lead 14 during insertion of the lead into the heart 10 as well as subsequent removal of the lead from the heart.

Figure 3:
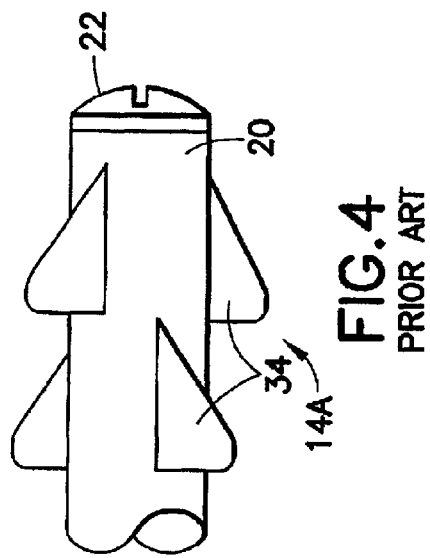
FIG. 3 is a detail side elevation view of the distal end of a lead system as that illustrated in FIGS. 1 and 2.

As seen in FIGS. 1, 2, and 3, passive fixation pacing or defibrillation leads such as the illustrated leads 14 employ tines 18 as a means of fixating its distal electrode 22 into the endocardium to prevent micro-dislodgment and thereby maintaining relatively stable capture and sensing values. Even though the silicone rubber based tines 18 fold back on themselves when fed through an introducer (not shown) at implantation, tines tend to dictate the size of the introducer employed. In keeping up with the demand in the industry for pacing and defibrillation leads and catheters with smaller French sizes, minimizing the overall size of future lead designs is warranted.

Figure 4:
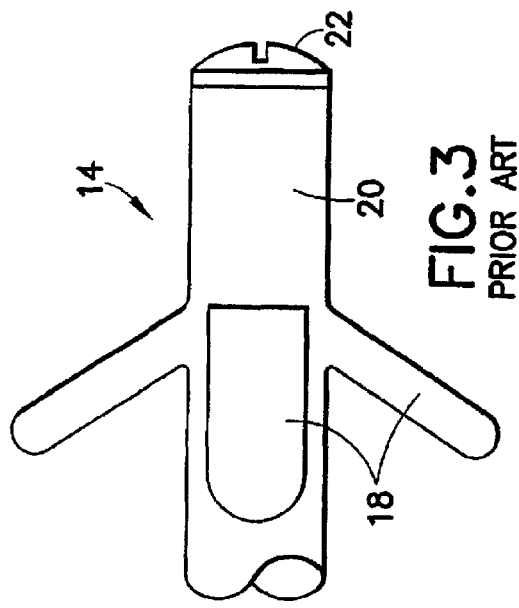
FIG. 4 is a detail side elevation view of the distal end of a known lead system illustrating another known construction for fixating the distal electrode into the endocardium.

A modified lead 14A is illustrated in FIG. 4 which employs a plurality of longitudinally and circumferentially spaced fins 34 which may be used alternatively to the tines 18 in a known manner.

Although the present invention will be described with reference to the embodiments shown in the drawings, it should be understood that the present invention can be embodied in many alternate forms or embodiments. In addition, any suitable size, shape or type of elements or materials suitable for the invention could be used.

Figure 5:
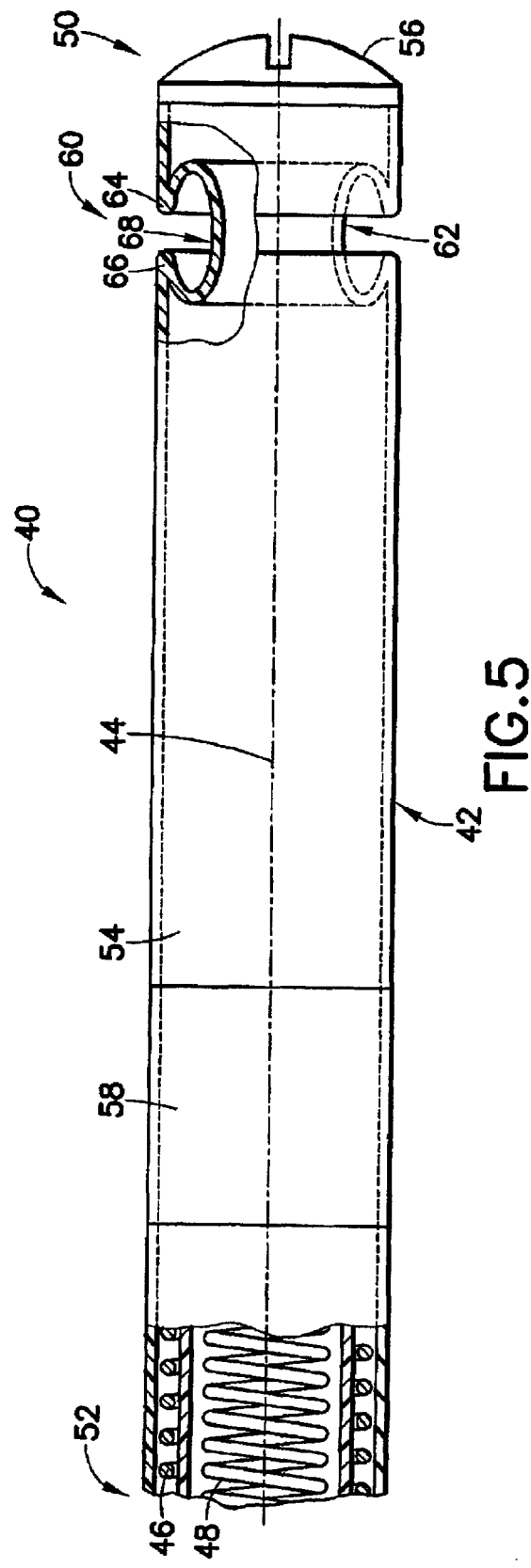
FIGS. 5–12 are detail side elevation views of the distal end of a lead system, each illustrating a modified construction according to the invention, of the distal end of a lead for fixating the distal electrode into the endocardium.

Turn now to FIG. 5 for the description of a first embodiment of the invention. In this instance, an implantable cardiac stimulation bipolar lead system 40 for use with an implantable stimulation device such as the pacemaker 28 typically includes an elongated lead 42 having a longitudinal axis 44 and including first and second mutually insulated conductors 46, 48 extending between a distal end 50 and a proximal end 52. A tubular insulating sheath 54 has an outer peripheral surface of revolution defined by a radius originating at the longitudinal axis 44. A tip electrode 56 at the distal end 50 of the lead 42 is attached to the second conductor 48 in a known and suitable manner. A ring electrode. 58 is proximally spaced from the tip electrode 56 and is suitably attached to the first conductor 46. A proximal connector such as that indicated by reference numeral 24 in FIG. 2 is in electrical continuity with the stimulation device as indicated by the pacemaker 28 and is coupled, respectively, to the tip electrode 56 and to the ring electrode 58.

The tubular insulating sheath 54 which overlies the interior of the lead 42 is formed with a passive fixation feature 60 formed into the outer peripheral surface of the sheath 54 and, in accordance with the invention, serves to encourage tissue ingrowth to facilitate stability of the tip electrode when the lead system is implanted. A distinguishing characteristic of the invention resides in the construction according to which no portion of the passive fixation feature 60 extends radially from the longitudinal axis 44 by a distance greater than the radius of the tubular insulating sheath 54. In short, no part of the feature 60 projects beyond the outer peripheral surface of the insulating sheath.

In more detail, the passive fixation feature 60 is comprised of an annular cavity 62 spaced proximally from the tip electrode 56 and distally from the ring electrode 58. It is further defined by a distally facing annular lip 64 adjacent the outer peripheral surface of the insulating sheath 54, a proximally facing annular lip 66 adjacent the outer peripheral surface spaced from and opposed to the distally facing annular lip, and an intermediate continuous concavely curved annular surface 68 extending between the annular lips 64, 66. A maximum radial dimension between a plane of the outer peripheral surface of the insulating sheath 54 and the concavely curved annular surface 68 is less than the longitudinal dimension of the concavely curved annular surface 68.

Figure 6:
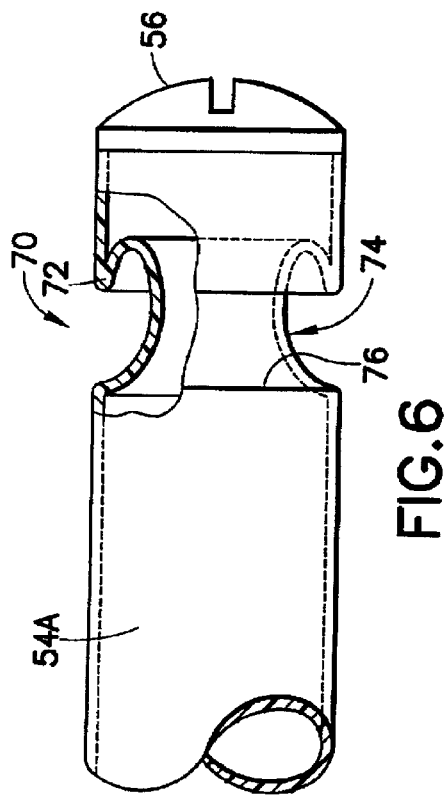

Another embodiment of the invention is illustrated in FIG. 6. In this instance, a modified passive fixation feature 70 is defined by a proximally facing annular lip 72 adjacent the outer peripheral surface of a modified insulating sheath 54A and a continuous concavely curved annular surface 74 which extends proximally from the annular lip 72 and intersects with the outer peripheral surface of the insulating sheath at an annular edge 76. The proximally facing annular lip 72 is spaced from and opposed to the annular edge 76.

Figure 7:
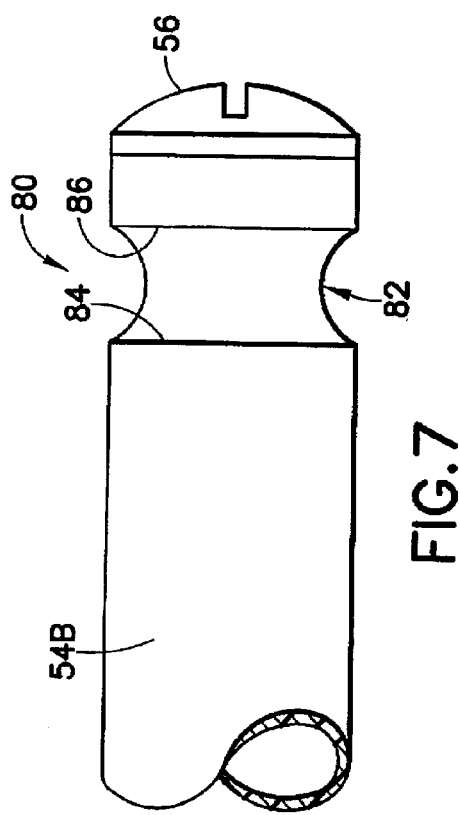

Still another embodiment of the invention is illustrated in FIG. 7. In this instance, a modified passive fixation feature 80 is defined by a continuous concavely curved annular surface 82 intersecting with the outer peripheral surface of a modified insulating sheath 54B, respectively, at a proximal annular edge 84 and at a distal annular edge 86. The annular edges 84, 86 are longitudinally spaced apart.

Figure 8:
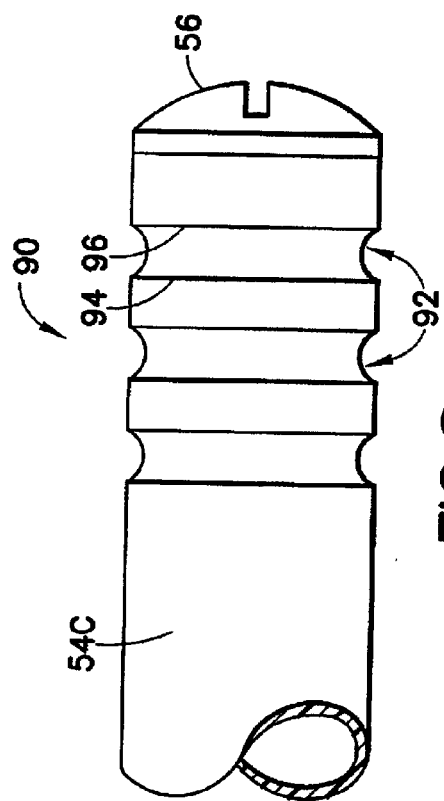

Yet another embodiment of the invention is illustrated in FIG. 8. In this instance, a modified passive fixation feature 90 is defined by a plurality of continuous concavely curved annular surfaces 92. Each of the concavely curved annular surfaces 92 intersects with the outer peripheral surface of a modified insulating sheath 54C, respectively, at a proximal annular edge 94 and at a distal annular edge 96. The annular edges 94, 96 are longitudinally spaced apart and the concavely curved annular surfaces 92 are also longitudinally spaced from one another.

Figure 9:
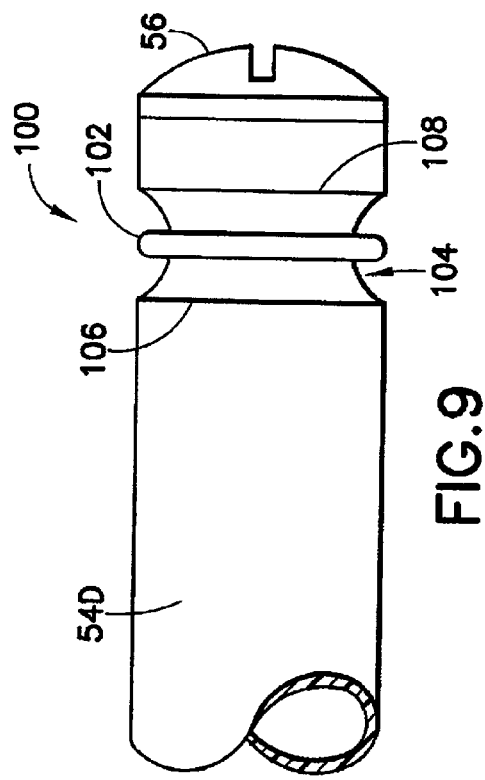

Still a further embodiment of the invention is illustrated in FIG. 9. In this instance, a modified passive fixation feature 100 is defined by an annular rim 102 projecting radially from a concavely curved annular surface 104 intermediate a proximal annular edge 106 and a distal annular edge 108.

Figure 10:
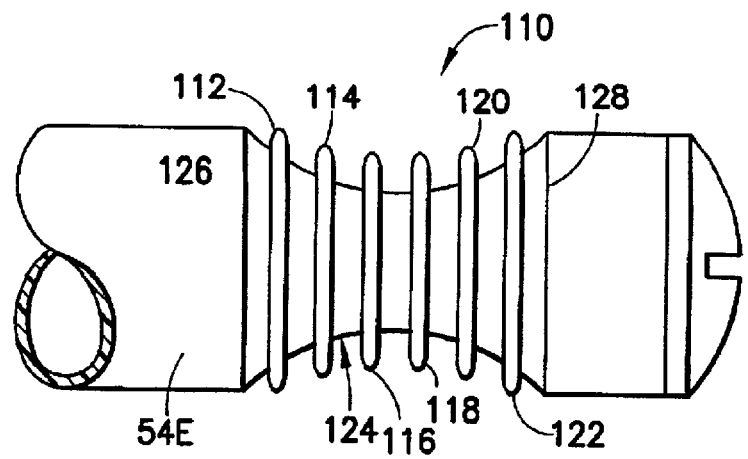

Yet a further embodiment of the invention is illustrated in FIG. 10. In this instance, a modified passive fixation feature 110 is defined by a plurality of annular rims 112, 114, 116, 118, 120, 122 all of which lie in parallel planes and project radially from a concavely curved annular surface 124 at longitudinally spaced locations intermediate a proximal annular edge 126 and a distal annular edge 128.

Figure 11:
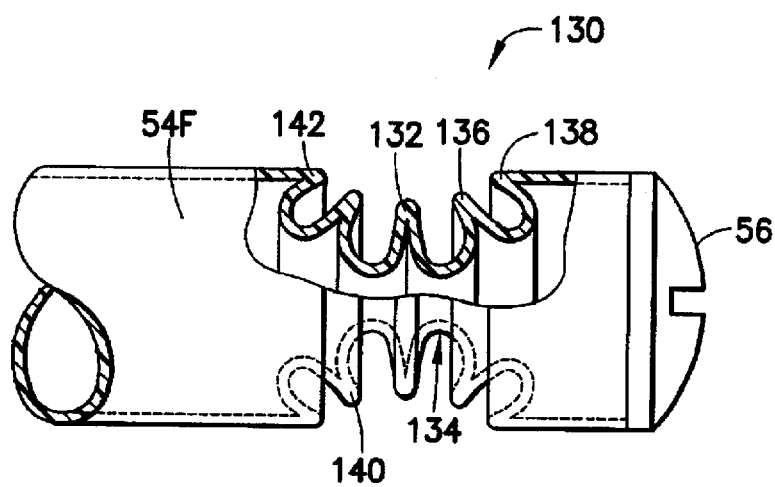

Still another embodiment of the invention is illustrated in FIG. 11. In this instance, a modified passive fixation feature 130 is defined by a central annular rim 132 which lies in a plane perpendicular to a longitudinal axis of the lead and projects radially from a concavely curved annular surface 134 intermediate the longitudinal dimension of the concavely curved annular surface. One annular rim 136 lies intermediate the central annular rim 132 and a proximally facing lip 138 and lies in a conical distally facing plane. Another annular rim 140 lies intermediate the central annular rim 132 and a distally facing lip 142 and lies in a conical distally facing plane.

Figure 12:
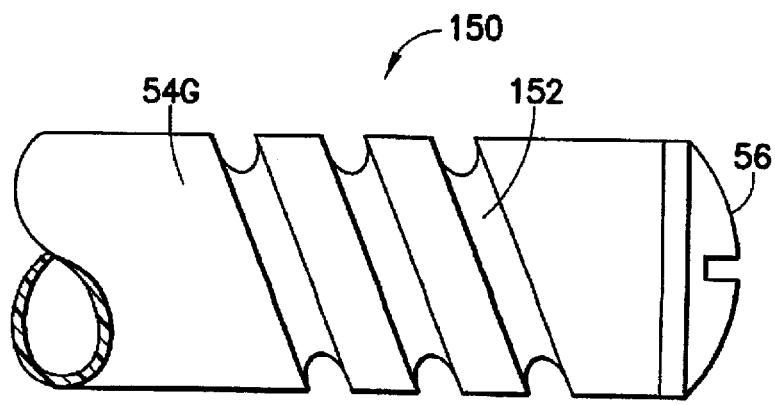

Yet a further embodiment of the invention is illustrated in FIG. 12. In this instance, a modified passive fixation feature 150 is defined by a helical groove 152 coaxial with the outer peripheral surface of a modified insulating sheath 54G.

In each instance described, a lead system is provided with a passive fixation feature formed into the outer peripheral surface of the insulation sheath for encouraging tissue ingrowth to facilitate stability of the tip electrode when the lead system is implanted. No portion of the feature extends radially from the longitudinal axis by a distance greater than the radius of the tubular insulating sheath. While a lead system employing the invention will be firmly fixated into the endocardium, its design facilitates extraction of the lead should the need arise.

It should be understood that the foregoing description is only illustrative of the invention. Various alternatives and modifications can be devised by those skilled in the art without departing from the invention. For example, while the invention has been described in combination with a bipolar lead system, it could just as readily be applied to a monopolar lead system. Accordingly, the present invention is intended to embrace all such alternatives, modifications and variances which fall within the scope of the appended claims.

What is claimed is:

1. An implantable cardiac stimulation lead system for use with an implantable stimulation device, the lead system comprising:
   an elongated lead having a longitudinal axis and including a conductor extending between a distal end and a proximal end of the lead;
   a tubular insulating sheath overlying the conductor and having an outer peripheral surface of revolution defined by a radius originating at the longitudinal axis;
   a tip electrode at the distal end of the lead attached to the conductor;
   a proximal connector in electrical continuity with the stimulation device and coupled to the conductor;
   the tubular insulating sheath formed with a passive fixation feature formed into the outer peripheral surface for encouraging tissue ingrowth, wherein no portion of the passive fixation feature extends radially from the longitudinal axis by a distance greater than the radius of the tubular insulating sheath and wherein the passive fixation feature is defined by a distally facing annular lip adjacent the outer peripheral surface, a proximally facing annular lip adjacent the outer peripheral surface spaced from and opposed to the distally facing annular lip, and an intermediate continuous concavely curved annular surface extending between the distally facing annular lip and the proximally facing annular lip, a maximum radial dimension between a plane of the outer peripheral surface and the concavely curved annular surface being less than the longitudinal dimension of the concavely curved annular surface.

2. An implantable cardiac stimulation lead system for use with an implantable stimulation device, the lead system comprising:
   an elongated lead having a longitudinal axis and including a conductor extending between a distal end and a proximal end of the lead;
   a tubular insulating sheath overlying the conductor and having an outer peripheral surface of revolution defined by a radius originating at the longitudinal axis;
   a tip electrode at the distal end of the lead attached to the conductor;

a proximal connector in electrical continuity with the stimulation device and coupled to the conductor;

the tubular insulating sheath formed with a passive fixation feature formed into the outer peripheral surface for encouraging tissue ingrowth, wherein no portion of the passive fixation feature extends radially from the longitudinal axis by a distance greater than the radius of the tubular insulating sheath and wherein the passive fixation feature is defined by a proximally facing annular lip adjacent the outer peripheral surface and a continuous concavely curved annular surface extending proximally from the proximally facing annular lip and intersecting with the outer peripheral surface at an annular edge, the proximally facing annular lip being spaced from and opposed to the annular edge.

3. An implantable cardiac stimulation lead system for use with an implantable stimulation device, the lead system comprising:

an elongated lead having a longitudinal axis and including first and second mutually insulated conductors extending between a distal end and a proximal end;

a tubular insulating sheath having an outer peripheral surface of revolution defined by a radius originating at the longitudinal axis;

a tip electrode at the distal end of the lead attached to the first conductor;

a ring electrode proximally spaced from the tip electrode attached to the second conductor;

a proximal connector in electrical continuity with the stimulation device and coupled, respectively, to the tip electrode and to the ring electrode;

wherein the tubular insulating sheath is formed with a passive fixation feature formed into the outer peripheral surface for encouraging tissue ingrowth to facilitate stability of the tip electrode when the lead system is implanted, no portion of which extends radially from the longitudinal axis by a distance greater than the radius of the tubular insulating sheath and wherein the passive fixation feature is defined by a distally facing annular lip adjacent the outer peripheral surface, a proximally facing annular lip adjacent the outer peripheral surface spaced from and opposed to the distally facing annular lip, and an intermediate continuous concavely curved annular surface extending between the distally facing annular lip and the proximally facing annular lip, a maximum radial dimension between a plane of the outer peripheral surface and the concavely curved annular surface being less than the longitudinal dimension of the concavely curved annular surface.

4. An implantable cardiac stimulation lead system for use with an implantable stimulation device, the lead system comprising:

an elongated lead having a longitudinal axis and including first and second mutually insulated conductors extending between a distal end and a proximal end;

a tubular insulating sheath having an outer peripheral surface of revolution defined by a radius originating at the longitudinal axis;

a tip electrode at the distal end of the lead attached to the first conductor;

a ring electrode proximally spaced from the tip electrode attached to the second conductor;

a proximal connector in electrical continuity with the stimulation device and coupled, respectively, to the tip electrode and to the ring electrode;

wherein the tubular insulating sheath is formed with a passive fixation feature formed into the outer peripheral surface for encouraging tissue ingrowth to facilitate stability of the tip electrode when the lead system is implanted, no portion of which extends radially from the longitudinal axis by a distance greater than the radius of the tubular insulating sheath and wherein the passive fixation feature is defined by a proximally facing annular lip adjacent the outer peripheral surface and a continuous concavely curved annular surface extending proximally from the proximally facing annular lip and intersecting with the outer peripheral surface at an annular edge, the proximally facing annular lip being spaced from and opposed to the annular edge.

* * * * *